(12) United States Patent
Jiang et al.

(10) Patent No.: US 8,943,367 B2
(45) Date of Patent: Jan. 27, 2015

(54) METHOD FOR METRIC RANKING IN INVARIANT NETWORKS OF DISTRIBUTED SYSTEMS

(71) Applicant: NEC Laboratories America, Inc., Princeton, NJ (US)

(72) Inventors: Guofei Jiang, Princeton, NJ (US); Min Ding, Chalfont, PA (US); Yong Ge, Harrison, NJ (US)

(73) Assignee: NEC Laboratories America, Inc., Princeton, NJ (US)

( * ) Notice: Subject to any disclaimer, the term of this patent is extended or adjusted under 35 U.S.C. 154(b) by 226 days.

(21) Appl. No.: 13/738,004

(22) Filed: Jan. 10, 2013

(65) Prior Publication Data

US 2013/0219223 A1 Aug. 22, 2013

Related U.S. Application Data

(60) Provisional application No. 61/585,291, filed on Jan. 11, 2012.

(51) Int. Cl.
  *G06F 11/00* (2006.01)
  *G06F 11/07* (2006.01)
  *G06F 11/34* (2006.01)
  *G06F 19/24* (2011.01)

(52) U.S. Cl.
  CPC .......... *G06F 11/079* (2013.01); *G06F 11/3457* (2013.01); *G06F 19/24* (2013.01)
  USPC .......................................... 714/37

(58) Field of Classification Search
  CPC ............................ G06F 11/3457; G06F 19/24
  See application file for complete search history.

(56) References Cited

U.S. PATENT DOCUMENTS

| 7,698,463 | B2 * | 4/2010 | Ogier et al. | 709/242 |
|---|---|---|---|---|
| 7,764,617 | B2 * | 7/2010 | Cain et al. | 370/238 |
| 2002/0062388 | A1 * | 5/2002 | Ogier et al. | 709/238 |
| 2004/0029553 | A1 * | 2/2004 | Cain | 455/403 |
| 2007/0245034 | A1 * | 10/2007 | Retana et al. | 709/238 |
| 2011/0173616 | A1 * | 7/2011 | Lattmann et al. | 718/1 |

* cited by examiner

*Primary Examiner* — Charles Ehne
(74) *Attorney, Agent, or Firm* — Joseph Kolodka; Akitaka Kimura

(57) ABSTRACT

A method for metric ranking in invariant networks includes, given an invariant network and a set of broken invariants, two ranking processes are used to determine and rank the anomaly scores of each monitoring metrics in large-scale systems. Operators can follow the rank to investigate the root-cause in problem investigation. In a first ranking process, given a node/metric, the method determines multiple scores by integrating information from immediate neighbors to decide the anomaly score for metric ranking. In a second ranking process, given a node/metric, an iteration process is used to recursively integrate the information from immediate neighbors at each round to determine its anomaly score for metric ranking.

10 Claims, 2 Drawing Sheets

METHOD FOR METRIC RANKING IN INVARIANT NETWORKS OF DISTRIBUTED SYSTEMS

This application claims the benefit of U.S. Provisional Application No. 61/585,291 filed Jan. 11, 2012, the disclosure of which is herein incorporated by reference.

BACKGROUND OF THE INVENTION

The invention relates generally to the field of fault detection and localization in complex systems. More specifically, the invention is related to a method for metric ranking in invariant networks of distributed systems.

In an existing system invariant analysis technology, invariants are discovered from monitoring data of large-scale distributed systems these invariants are further used for fault detection and isolation. Each invariant profiles a constant relationship between two monitoring metrics and the invariant network is consisted of these monitoring metrics as nodes and their invariants as edges. With this approach, when a fault occurs inside a large system, many invariants will break due to the dependency of its components. Now given the set of broken invariants at a time point, the key question is how to rank the anomaly of monitoring metrics so that system operators can follow the rank to investigate the root-case in problem troubleshooting.

In a previous patent, U.S. Pat. No. 7,590,513, there is described, only, uses of the ratio of broken invariants for metric ranking.

Accordingly, there is a need for a method for a metric ranking in invariant networks in distributed systems.

BRIEF SUMMARY OF THE INVENTION

The present invention provides a method for metric ranking in invariant networks includes, given an invariant network and a set of broken invariants, two ranking processes are used to determine and rank the anomaly scores of each monitoring metrics in large-scale systems. Operators can follow the rank to investigate the root-cause in problem investigation. In a first ranking process, given a node/metric, the method determines multiple scores by integrating information from immediate neighbors to decide the anomaly score for metric ranking. In a second ranking process, given a node/metric, an iteration process is used to recursively integrate the information from immediate neighbors at each round to determine its anomaly score for metric ranking.

These and other advantages of the invention will be apparent to those of ordinary skill in the art by reference to the following detailed description and the accompanying drawings.

DETAILED DESCRIPTION

Figure 1:
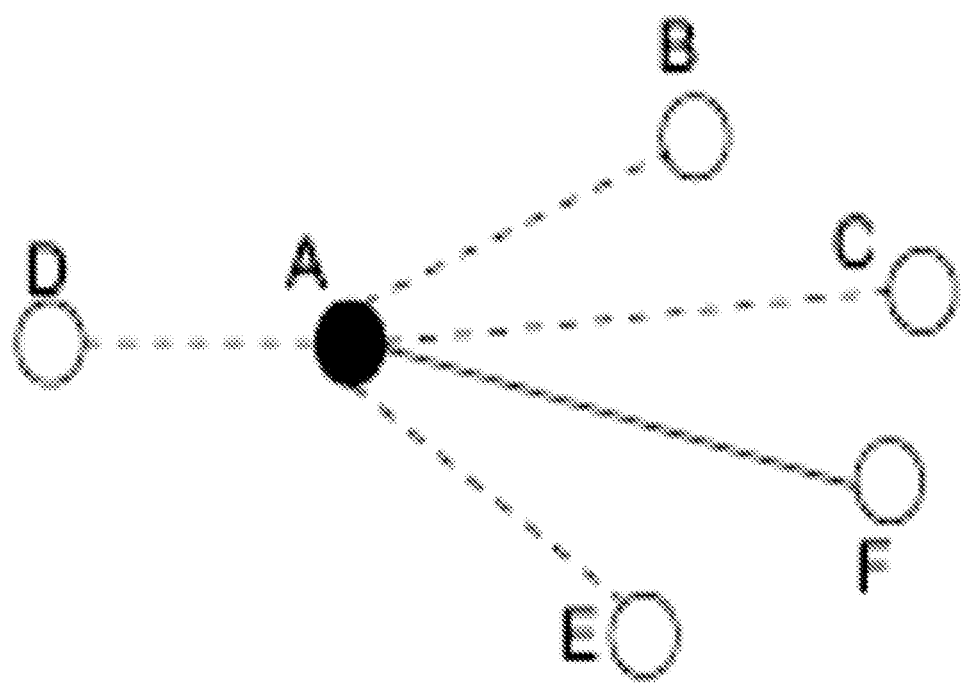
FIG. 1 depicts nodes representing monitoring metrics, in accordance with the invention.

The invention is directed to a method for metric ranking in invariant networks of distributed systems. The invariant network consists of monitoring metrics as nodes and invariant pair wise relationships of these nodes as edges. In the FIG. 1, the nodes A-F are the monitoring metrics such as CPU utilization, memory usage and volume of network packets etc. The edge represents the invariant between two associated nodes. At a time point, when a fault occurs, the broken invariant is represented by the dashed line and the good invariant is represented by the solid line. The inventive method employs a graph analysis and uses the neighborhood information to support the analysis of anomaly ranking. For example, the inventive method not only uses the ratio of broken invariants associated with A (among 5 invariants, 4 are broken) to rank its abnormal level but it also uses the broken invariant information from its neighbor (B-F here) to calculate the anomaly score of node A. In other words, the inventive method uses its immediate neighbor's information to support a node's anomaly ranking.

The framework for the invention is totally different from existing approaches so that there is no similar problem in other approaches. Although the problem of ranking is common in many areas such as webpage ranking in search engine results, the invariant network context for this invention includes thoroughly different invariant information and the goal of the inventive ranking method is also different.

Under the inventive method, given the invariant network and the set of broken invariants, two ranking processes are provided to determine and rank the anomaly scores of each monitoring metrics in large-scale systems. Operators can follow the rank to investigate the root-cause in a problem investigation. In an mRank process, given a node/metric, the invention determines multiple scores by integrating information from immediate neighbors to decide the anomaly score for metric ranking. In a gRank process, given a node/metric, an iteration process is used to recursively to integrate the information from immediate neighbors at each round to determine its anomaly score for metric ranking. A key inventive aspect is mRank and gRank processes include the step of integrating its anomaly score with its immediate neighbors' anomaly scores to decide their mutual influences on their anomaly scores so that the updated anomaly score is more accurate for metric ranking.

Figure 2:
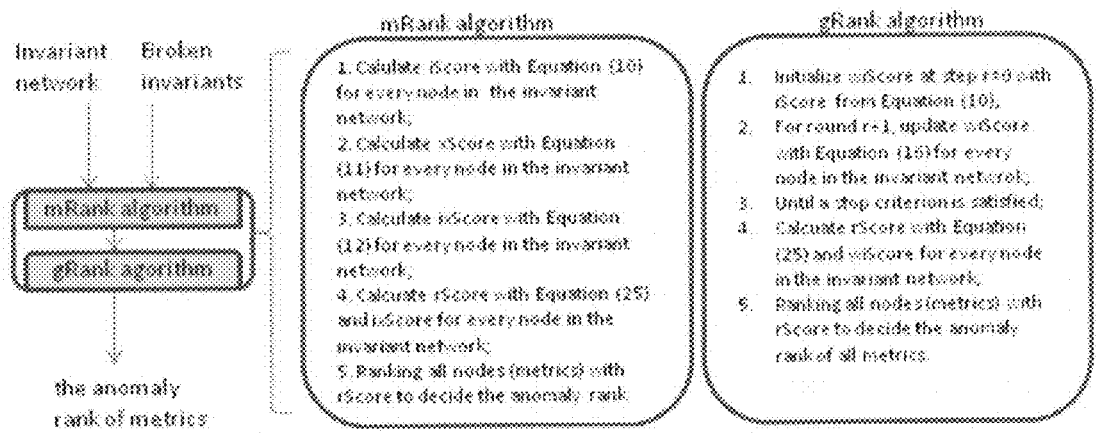
FIG. 2 shows the steps for metric ranking in an invariant network of a distributed system, in accordance with the invention.

Referring now to the block diagram of FIG. 2, there are shown the steps for metric ranking in an invariant network of a distributed system, in accordance with the invention. Invariant network information along with broken invariants are first analyzed under an mRank process and then under a gRank process. The mRank process includes quantifying steps eventually used to measure the anomaly degree each node in an invariant network. The gRank process, a weighted score mechanism, is an iterative process to determine a score to quantify the anomaly degree of each node. After both the mRank and gRank processes are applied, an anomaly rank of metrics is obtained.

Under the mRank process, in a first step, an iScore is based on the relationship (10) for every node in the invariant network. Relationship (10) defines the iScore of a node, $V_i$ ($1 \le i \le N$), within an invariant network I according to the relationship:

$$iScore_{V_i} = \frac{\text{number of broken links of } V_i}{\text{number of all links of } V_i}. \quad (10)$$

Then, under a second step, an xScore is determined based on the relationship (11) for every node in the invariant network. Relationship (11) defines an xScore of a node, $V_i$ ($1 \le i \le N$), within an invariant network I according to the relationship:

$$xScore_{V_i} = 1 - \frac{\text{number of broken links related to } BINNs}{\text{number of all links related to } BINNs}, \quad (11)$$

where BINNs represents broken-invariant-neighboring-nodes. The broken-invariant-neighboring-nodes of a node are those nodes, each of which connects to this node with a broken link. Note that, if one link is rerlated to multiple nodes of BINNs, the invention only counts this link once for xScore.

Under a third step of the mRank process, there is a determination of iScore based on the relationship (12), ixScore=iScore+xScore, for every node in the invariant network. This ixScore is used to measure the anomaly degree of each node in an invariant network. From the above definitions, it can be seen that ixScore combines multiple evidences from a node itself and its neighbors to infer its anomaly degree. The anomaly degree of a node cannot be inferred independently, because the node itself and its neighbors naturally influence each other. In fact, all the nodes directly or indirectly influence each other through the network. However, we only quantify the influence of the first-order neighbors for a node in this invention Under a $4^{th}$ step of the mRank process, an rScore is based on the relationship $$rScore(V_i) = \frac{\sum_{k=1}^{K} r_{ia_k}}{K}. \quad (25)$$

Suppose for a node Vi with K related broken links, we get K ratios $r_{iak}$ (1_k_K), where ak is the node index. This means that the node Vak is connected to node Vi via a broken link. For example, For example, if we get three ratios, $r_{ia1}$, $r_{ia2}$ and $r_{ia3}$, for a node then, the rScore of $V_i$ is rScore($V_i$)=($r_{ia1}$+$r_{ia2}$+$r_{ia3}$)/3. In the above definition of rScore, we use the average of all ratios as rScore.

In the fifth step under the mRank process, the method ranks all nodes (metrics) with rScore to decide the anomaly rank.

Turning now to the first step of the gRank process, wiScore is initialized at step r=0 with iScore from relationship (10) above. The parameter wiScore is a weighted iScore. With the definition of iScore, we can determine the iScore for each node. Then, the iScore of one node is highly reliable if all iScores of its BINNs are relatively low. The wiScore of a node, $V_i$ ($1 \le i \le N$), within an invariant network I is based on the relationship $$wiScore_{V_i} = \frac{\sum_{V_k \in BINNs \text{ of } V_i} (1 - iScore_{V_k}) * 1}{\text{number of all links of } V_i}, \quad (15)$$

where $V_k$ denotes an individual node of BINNs of node $V_i$.

In the second step of the gRank process, for round r=1, wiScore is updated with relationship (16) for every node in the invariant network. Relationship (16) is based on $$wiScore_{V_i}^{r+1} = \frac{\sum_{V_k \in BINNs \text{ of } V_i} (1 - wiScore_{V_k}^{r}) * 1}{\text{number of all links of } V_i}, \quad (16)$$

where $wiScore_{V_i}^{r+1}$ denotes the wiScore of node $V_i$ at the end of round r+1 iteration.

The update of wiScore for round r+1 is continued until a stop criterion is satisfied.

In the $4^{th}$ step of the gRank process, there is a determination of rScore with equation (25) and a determination of wiScore for every node in the invariant network.

In the $5^{th}$ step, there is a ranking of all (nodes (metrics) with rScore to decide the anomaly rank of all metrics.

Figure 3:
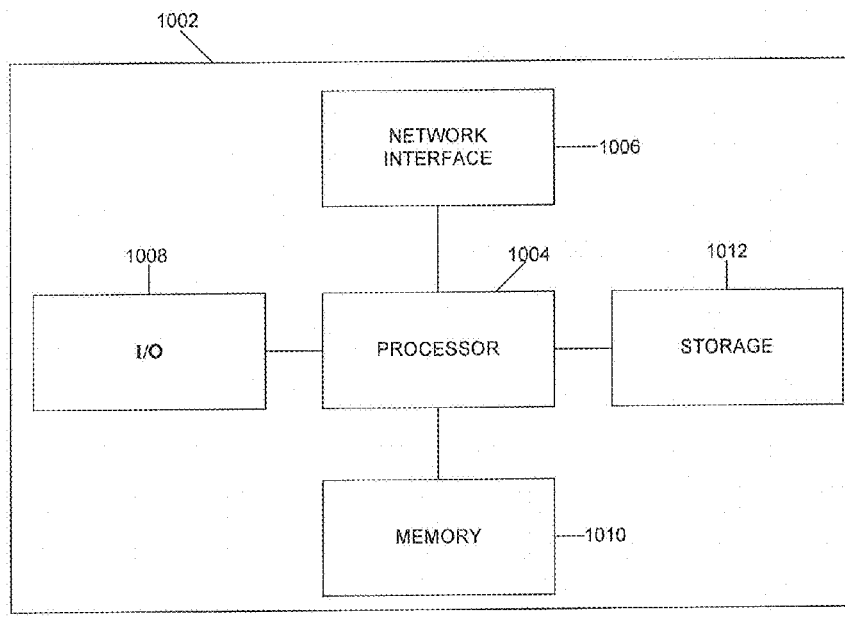
FIG. 3 shows a high level block diagram of a computer capable of implementing embodiments of the present invention.

The steps of the methods described herein may be performed by computers containing processors which are executing computer program code which defines the functionality described herein. Such computers are well known in the art, and may be implemented, for example, using well known computer processors, memory units, storage devices, computer software, and other components. A high level block diagram of such a computer is shown in FIG. 3. Computer 1002 contains a processor 1004 which controls the overall operation of computer 1002 by executing computer program instructions which define such operation. The computer program instructions may be stored in a storage device 1012 (e.g., magnetic disk) and loaded into memory 1010 when execution of the computer program instructions is desired. Thus, the operation of computer 1002 is defined by computer program instructions stored in memory 1010 and/or storage 1010 and the computer 1002 will be controlled by processor 1004 executing the computer program instructions. Computer 1002 also includes one or more network interfaces 906 for communicating with other devices via a network. Computer 1002 also includes input/output 1008 which represents devices which allow for user interaction with the computer 1002 (e.g., display, keyboard, mouse, speakers, buttons, etc.). One skilled in the art will recognize that an implementation of an actual computer will contain other components as well, and that FIG. 3 is a high level representation of some of the components of such a computer for illustrative purposes. One skilled in the art will also recognize that the functionality described herein may be implemented using hardware, software, and various combinations of hardware and software.

From the foregoing it can be appreciated that the inventive method for metric ranking improves the accuracy of anomaly metric ranking so that system operators can follow the rank to locate the root-cause quicker and spend less time and cost in incident investigation. Unlike the teachings of prior U.S. Pat. No. 7,590,513 where a ratio of broken invariants is considered, example looking at FIG. 1, the anomaly score of node A is 4/5, i.e. 4 invariants among total 5 invariants are broken. In the present inventive metric ranking method with mRank and gRank, the anomaly scores of its immediate neighbor (B-F here) are also used to influence the metric ranking of node A. Details on how to pull such neighbors' anomaly scores to determine node A's anomaly score are detailed in the appended "Additonal Information" document which explains equations 11, 12, 16 and 25 regarding pulling neighbors' anomaly scores to determine A's anomaly scores.

The Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. Additional information is provided in an appendix to the application entitled, "Additional Information". It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for metric ranking in invariant networks, the method comprising:
considering an invariant network and a set of broken invariants in said invariant network;
under first process, given a node/metric of said invariant network, determining multiple scores by integrating information from immediate neighboring nodes of said node to decide an anomaly score of said node for metric ranking; and
under a second process, given a node/metric of said invariant network, using an iteration to recursively integrate information from immediate neighboring nodes of said at each round to determine an anomaly score of said node for metric ranking,
wherein said first and second process facilitate a determination and ranking of said anomaly scores of each monitoring metrics in large scale invariant network systems for enabling following said ranking to investigate a problem in said invariant network, and
wherein said first process comprises determining an iScore for every node in the invariant network, said iScore of a node, $V_i(1<i<N)$, within an invariant network I being based on $$iScore_{V_i} = \frac{\text{number of broken links of } V_i}{\text{number of all links of } V_i}.$$

2. The method of claim 1,
wherein said first process comprises determining an ixScore for every node in the invariant network,
said ixScore being used to measure anomaly degree of each node in said invariant network, and
said ixScore combining multiple evidences from a node itself and its neighboring nodes to infer its anomaly degree.

3. The method of claim 1,
wherein said first process comprises determining an rScore is based on $$rScore(V_i) = \frac{\sum_{k=1}^{K} r_{ia_k}}{K},$$

where for a node Vi with K related broken links, there are K ratios $r_{ia_k}$ (1_k_K),
where ak is the node index which means that the node Vak is connected to node Vi via a broken link.

4. The method of claim 1,
wherein said second process comprises determing wiScore, which is a weighted iScore,
said wiScore of a node, $V_i(1 \geq i \geq N)$, within an invariant network I being based on $$wiScore_{V_i} = \frac{\sum_{V_k \in BINNs \text{ of } V_i} (1 - iScore_{V_k}) * 1}{\text{number of all links of } V_i},$$

where $V_k$ denotes an individual node of BINNs of node $V_i$ and BINNs represents broken-invariant-neighboring-nodes of a node, each of which connects to said node with a broken link.

5. The method of claim 4,
wherein said second process comprises wiScore being updated for every node in said invariant network based on $$wiScore_{V_i}^{r+1} = \frac{\sum_{V_k \in BINNs \text{ of } V_i} (1 - wiScore_{V_k}^{r}) * 1}{\text{number of all links of } V_i},$$

where $wiScore_{V_i}^{r+1}$ denotes the wiScore of node $V_i$ at the end of round r+1 iteration.

6. A method for metric ranking in invariant networks, the method comprising:
considering an invariant network and a set of broken invariants in said invariant network;
under first process, given a node/metric of said invariant network, determining multiple scores by integrating information from immediate neighboring nodes of said node to decide an anomaly score of said node for metric ranking; and
under a second process, given a node/metric of said invariant network, using an iteration to recursively integrate information from immediate neighboring nodes of said at each round to determine an anomaly score of said node for metric ranking,
wherein said first and second process facilitate a determination and ranking of said anomaly scores of each monitoring metrics in large scale invariant network systems for enabling following said ranking to investigate a problem in said invariant network, and
wherein said first process comprises determining an xScore for every node in the invariant network, said xScore of a node, $V_i(1 \geq i \geq N)$, within an invariant network I being based on $$xScore_{V_i} = 1 - \frac{\text{number of broken links related to } BINNs}{\text{number of all links related to } BINNs},$$

where BINNs represents broken-invariant-neighboring-nodes of a node, each of which connects to said node with a broken link.

7. The method of claim 6,
wherein said first process comprises determining an ixScore for every node in the invariant network,
said ixScore being used to measure anomaly degree of each node in said invariant network, and
said ixScore combining multiple evidences from a node itself and its neighboring nodes to infer its anomaly degree.

8. The method of claim 6,
wherein said first process comprises determining an rScore is based on $$rScore(V_i) = \frac{\sum_{k=1}^{K} r_{ia_k}}{K},$$

where for a node Vi with K related broken links, there are K ratios $r_{ia_k}$ (1_k_K),
where ak is the node index which means that the node Vak is connected to node Vi via a broken link.

9. The method of claim 6, wherein said second process comprises determining wiScore, which is a weighted iScore, said wiScore of a node, $V_i(1 \geq i \geq N)$, within an invariant network I being based on $$wiScore_{V_i} = \frac{\sum_{V_k \in BINNs \text{ of } V_i} (1 - iScore_{V_k}) * 1}{\text{number of all links of } V_i},$$

where $V_k$ denotes an individual node of BINNs of node $V_i$ and BINNs represents broken-invariant-neighboring-nodes of a node, each of which connects to said node with a broken link.

10. The method of claim 9, wherein said second process comprises wiScore being updated for every node in said invariant network based on $$wiScore_{V_i}^{r+1} = \frac{\sum_{V_k \in BINNs \text{ of } V_i} (1 - wiScore_{V_k}^r) * 1}{\text{number of all links of } V_i},$$

where $wiScore_{V_i}^{r+1}$ denotes the wiScore of node $V_i$ at the end of round r+1 iteration.

* * * * *